(12) United States Patent
Pichon et al.

(10) Patent No.: US 7,491,242 B2
(45) Date of Patent: Feb. 17, 2009

(54) FEMORAL PROSTHESIS

(75) Inventors: Denis Pichon, Mordelles (FR);
Christophe Cueille, Missy (FR);
Nicolas Delogé, Douvres (FR)

(73) Assignee: Benoist Girard SAS (FR)

( * ) Notice: Subject to any disclaimer, the term of this patent is extended or adjusted under 35 U.S.C. 154(b) by 673 days.

(21) Appl. No.: 10/795,946

(22) Filed: Mar. 8, 2004

(65) Prior Publication Data
US 2004/0199259 A1 Oct. 7, 2004

(30) Foreign Application Priority Data
Mar. 10, 2003 (GB) ................. 0305449.1

(51) Int. Cl.
*A61F 2/32* (2006.01)
(52) U.S. Cl. ................. 623/23.21; 623/23.46
(58) Field of Classification Search ............... 623/22.4, 623/22.41, 22.42, 22.43, 23.21, 23.22, 23.26, 623/23.44, 23.46, 22.46, 23.52, 19.11–19.14, 623/21.15; 606/61
See application file for complete search history.

(56) References Cited

U.S. PATENT DOCUMENTS

| | | | |
|---|---|---|---|
| 3,987,499 A * | 10/1976 | Scharbach et al. | ........ 623/22.46 |
| 4,790,852 A | 12/1988 | Noiles | |
| 4,846,839 A | 7/1989 | Noiles | |
| 5,092,900 A | 3/1992 | Marchetti et al. | |
| 5,108,452 A | 4/1992 | Fallin | |
| 5,201,769 A | 4/1993 | Schutzer | |
| 5,211,666 A | 5/1993 | Fetto | |
| 5,549,706 A | 8/1996 | McCarthy | |
| 5,766,262 A | 6/1998 | Mikhail | |
| 5,860,982 A | 1/1999 | Ro et al. | |
| 6,217,620 B1 * | 4/2001 | Park | ........ 623/23.26 |
| 6,706,073 B2 * | 3/2004 | Draenert et al. | ........ 623/23.26 |
| 2004/0024469 A1 * | 2/2004 | Ferree | ........ 623/23.26 |

FOREIGN PATENT DOCUMENTS

EP 1 013 241 A2 6/2000

* cited by examiner

*Primary Examiner*—Brian E. Pellegrino
(74) *Attorney, Agent, or Firm*—Lerner, David, Littenberg, Krumholz & Mentlik, LLP

(57) ABSTRACT

A femoral prosthesis including a stem for insertion in a femoral canal and a shoulder and/or neck portion characterized by a proximal sleeve having an outer circumferential wall and comprising two or more proximal sleeve components, each of which provides part of the circumferential outer surface of the sleeve, and means for securing the proximal sleeve components in position at the proximal end of the stem.

23 Claims, 9 Drawing Sheets

FEMORAL PROSTHESIS

BACKGROUND OF THE INVENTION

This invention relates to a femoral prosthesis which is for insertion into the bone canal of a femur and is particularly, although not exclusively, applicable for use in revision surgery.

When carrying out revision surgery it is usually necessary to provide rigid support of the proximal end of the bone canal due to this end of the canal tending to be flared out when the previous prosthesis was removed. It is known to provide a filling in this area and it is also known to provide a proximal sleeve on the prosthesis to accommodate the lack of bone.

With known sleeves it is difficult for the surgeon to judge the required tapering thickness of such a sleeve so that maximum support is obtained and, in any case, it is usually necessary for the sleeve to be attached to the stem of the prosthesis prior to assembly.

The present invention is intended to overcome some of the difficulties referred to above by providing a sleeve which can be fitted to a prosthesis before or after the stem of the prosthesis has been placed in position in the bone canal.

SUMMARY OF THE INVENTION

According to the present invention a femoral prosthesis includes a stem for insertion in a femoral canal and a shoulder and neck portion characterized by a proximal sleeve having an outer circumferential surface and comprising two or more proximal sleeve components, each of which provides part of the circumferential outer surface of the sleeve, and connector for securing the proximal sleeve components in position at the proximal end of the stem.

Thus, it is now possible for the surgeon to fix the stem in position in the bone canal and then add the two or more proximal sleeve components enabling him to use sleeve components which adequately fit the bone canal walls to provide a proximal sleeve of correct shape.

In one preferred construction, two proximal sleeve components are provided and which are located respectively on the medial and lateral sides of the stem. In another embodiment a lateral sleeve component is provided which also extends to the medial side of the stem and a medial sleeve component fastens to the lateral sleeve component to provide a clamp thereon. Alternatively, a medial sleeve component can be provided which also extends to the lateral side of the stem and a lateral sleeve component fastens to the medial sleeve component to provide a clamp thereon.

In another alternative construction two proximal sleeve components can be provided and which are located respectively on the posterior and anterior sides of the stem. Another alternative construction includes three or more proximal sleeve components which are provided which are arranged around the stem. The shoulder and/or neck portion can be separately attachable to the stem.

With all these arrangements each proximal sleeve component can be accompanied by one or more alternative sleeve components each of which is of the same interior shape but which has alternatively shaped part-circumferential outer surfaces. This provides a modular construction in which the final shape of the proximal sleeve can be varied to suit the patient.

Preferably the shoulder and/or neck portion of the stem is separately attachable to the stem before or after the stem has been inserted into the canal bone. The operating surgeon now therefore has a modular construction in which the appropriate sleeve portions and the shoulder and/or neck can be fitted to the stem after it has been inserted into the bone canal. The attachable shoulder and/or neck portion may conveniently be located on a taper on the proximal end of the stem and can be held in position by a screw or clip.

Preferably the shoulder and/or neck portion is provided with a connection element to attach a ball head or the ball head can be integral with the neck portion. Alternatively, the ball head can be integral with the shoulder and/or neck portion.

The various proximal sleeve components can be secured to the proximal end of the stem by any convenient attachment means, for example, they could be arranged to be held in place by screws which locate on the stem or locate on another proximal head portion to allow them to be pulled together into tight engagement or they could even be arranged to clip onto the stem.

The prosthesis can also include a support for the great trochanter which can be provided on one of more of the proximal sleeve portions and in a convenient arrangement the support is separately attachable to one of the proximal sleeve portions.

The surgeon may desire to fasten the various parts together before inserting the prosthesis into the bone canal and to enable him to select the correct shapes for the proximal sleeve components. The invention can include a femoral prosthesis as set forth above in combination with a ghost or trial prosthesis which comprises a trial stem for insertion into a femoral canal and a trial shoulder and/or neck portion and having a trial proximal sleeve having an outer circumferential wall and comprising two or more trial proximal sleeve components each of which provides part of the circumferential outer surface of the trial sleeve and a connection element for securing the trial proximal sleeve components in position at the proximal end of the trial stem, the trial proximal sleeve components being of the same dimensions and shapes as those provided with the femoral prosthesis.

Thus equipped the surgeon can make up a trial prosthesis by applying different shapes of sleeve components until he achieves what he regards as an ideal fit. Modular sleeve components of the same dimensions and shapes of those which he has selected for the ghost or trial prosthesis can now be applied to the femoral prosthesis itself before it is inserted into the bone.

As set forth above the neck portion can also be separately attachable to the same stem portion and the trial prosthesis will therefore include a similar attachable stem portion thus allowing a femoral prosthesis to be constructed which is identical with the trial prosthesis.

In an alternative arrangement, and according to a further aspect of the invention, a femoral prosthesis as set forth above can be provided in combination with a trial stem for insertion in a femoral canal and a trial shoulder and/or neck portion which is dimensioned and shaped to receive the proximal sleeve portions of the femoral prosthesis and a connector for detachably securing them in place at the proximal end of the trial stem. As before, a separate and attachable neck portion can be provided on the trial prosthesis.

The prosthesis can also include a projecting feature which can act to prevent subsidence of the stem when implanted and to act as a "landmark" and which is provided on one of the proximal sleeve components.

With this arrangement only one set of modular proximal sleeve component is required. They are first used on the trial prosthesis stem so that the surgeon can determine the precise shapes and proportions required and can then be transferred to the femoral prosthesis stem and neck thus again ensuring a precise fit.

The femoral prosthesis can be supplied as a kit in which there are a series of different sized femoral components and a series of different size trial prosthesis which include a trial stem for insertion into the femoral canal. A trial shoulder and/or neck portion can be provided and at least two proximal sleeve portions, each having an outer circumferential surface for placement adjacent the inner surface of the proximal medullary canal of the femur. The preferred kit would have a series of sleeve portions of varying sizes and shapes, each of which can be coupled to another sleeve portion and be clamped around the proximal circumferential outer surface of the trial stem with the sleeve portions being chosen to fill the proximal canal. In the preferred embodiment, the sleeve portions are clamped around the proximal stem outer circumference by having threaded bores in one sleeve component and non-threaded throughbores in the other sleeve component and using screws to clamp the sleeve portions around the stem. Of course, any means of developing a clamping force between the two sleeve components could be used. The kit could also include three or even four sleeve parts which can be assembled about the outer circumference of a single stem to produce the required filling of the proximal/femoral canal.

BRIEF DESCRIPTION OF THE DRAWINGS

The invention can be performed in various ways and some embodiments will now be described by way of example and with reference to the accompanying drawings in which.

DETAILED DESCRIPTION

Figure 1:
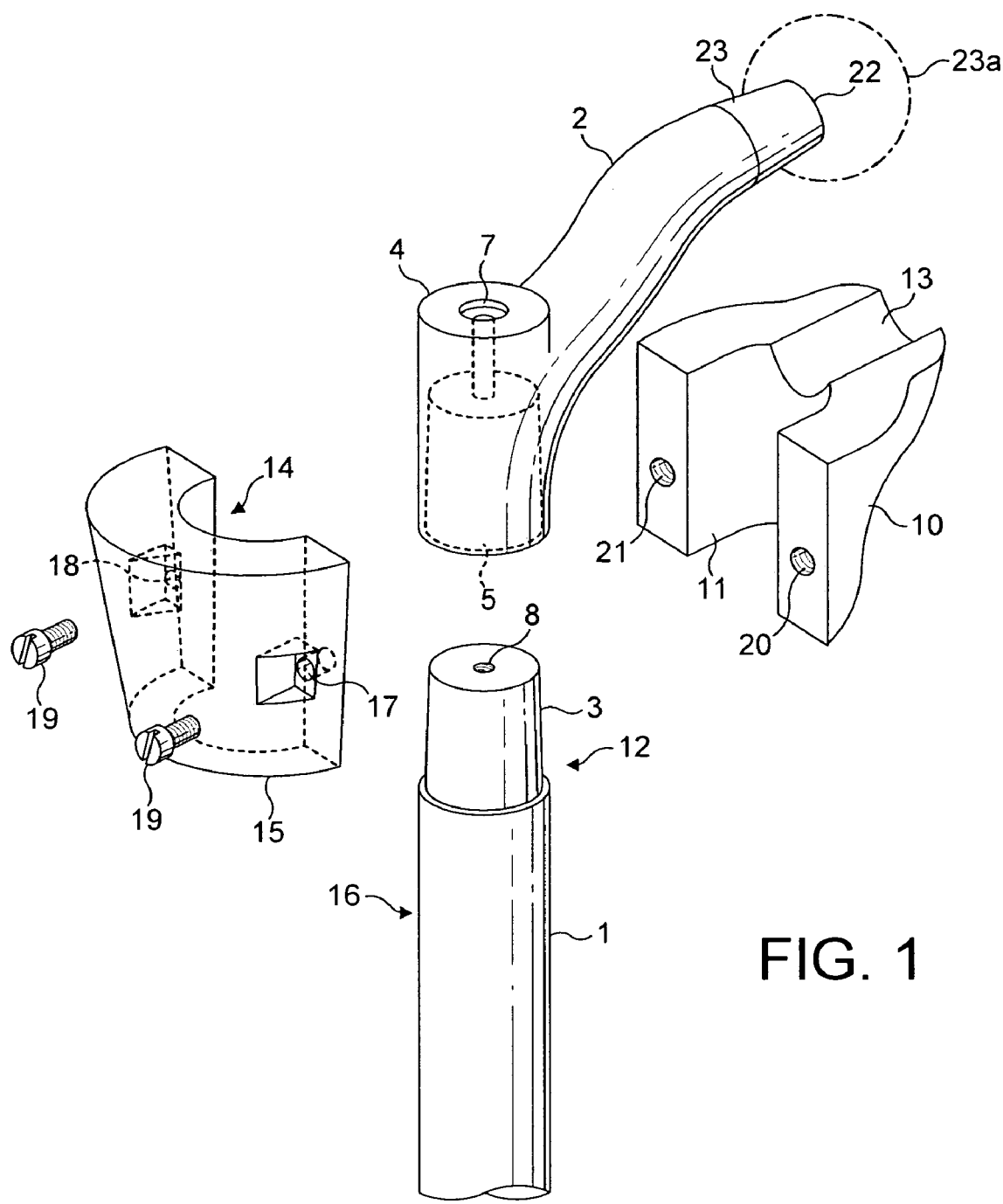
FIG. 1 is an exploded diagrammatic view of a prosthesis according to the present invention.
Figure 2:
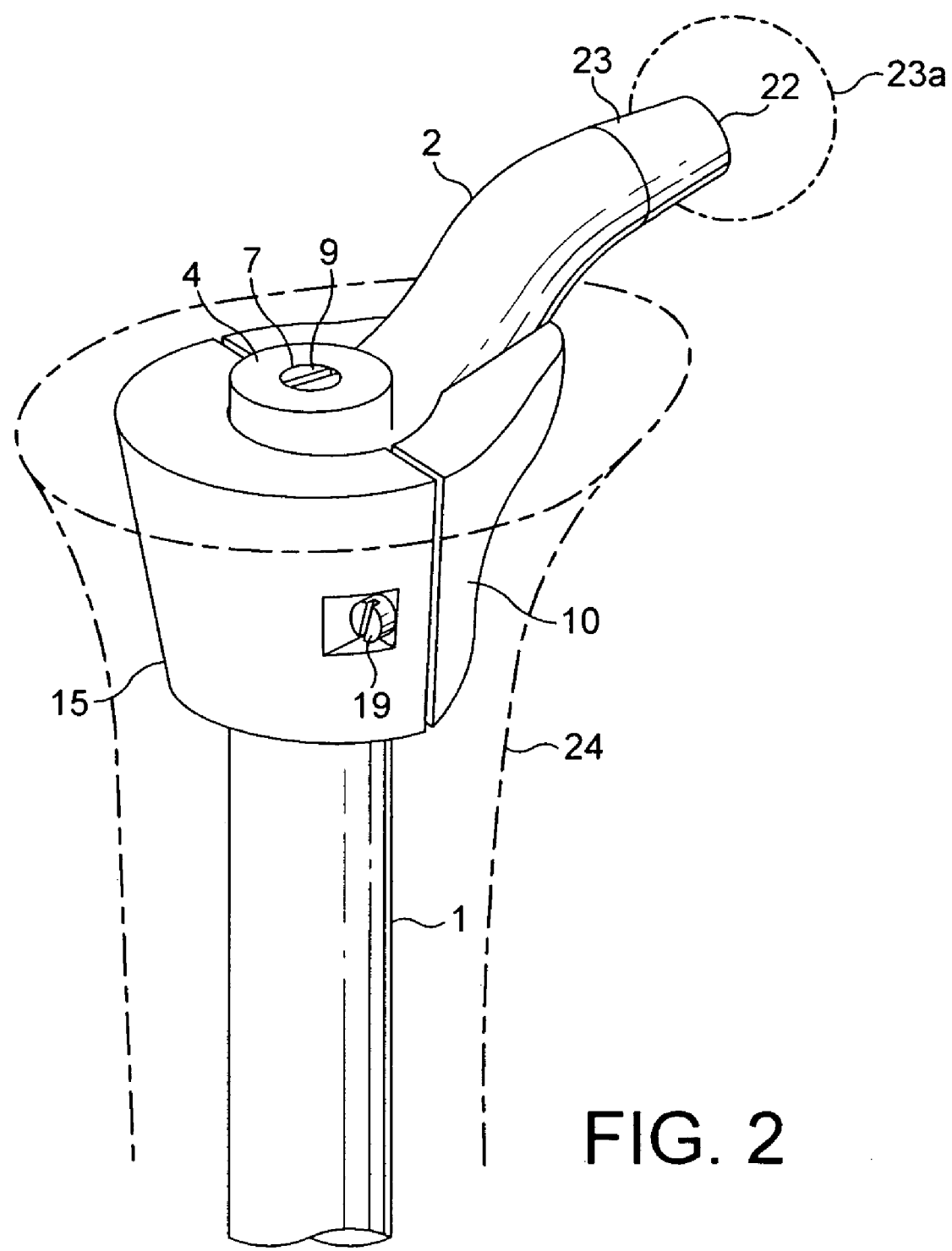
FIG. 2 is a pictorial isometric view of the femoral prostheses assembled from the parts shown in FIG. 1.

As shown in FIGS. 1 and 2 of the drawings a femoral prosthesis according to a preferred embodiment of the present invention comprises a stem 1 having a shoulder and/or neck portion 2. The proximal end of stem 1 has a tapered spigot or trunnion 3 and neck portion 2 has a raised boss 4 which provides a shoulder. Located within boss 4 is a tapered socket 5 which is shaped and dimensioned to locate on tapered spigot 3 of stem 1. A screw 9 (shown in FIG. 2) is provided which can extend through a flanged opening 7 in boss 4 and into a screw threaded opening 8 in spigot 3 to hold shoulder and/or neck portion 2 rigidly in position on stem 1. This stem 1 can be of any convenient and well known shape for use in a bone canal.

Included in the construction is a medial proximal sleeve component 10 which has a groove 11 which is shaped to cooperate with medial side 12 of stem 1 and neck portion 2. Sleeve component 10 also has a trough 13 to adapt it to the distal side of stem portion 2.

A proximal sleeve component 15 is also provided which has a groove 14 adapted to locate on lateral side 16 of the shoulder and neck portion 2 and stem 1. Screw openings 17 and 18 are provided in lateral proximal sleeve component 15 for the passage of grub screws 19 which can locate in appropriate screw threaded openings 20 and 21 in medial component 10 to firmly attach the proximal sleeve components in position when assembled. Free end 22 of the shoulder and/or neck portion 2 has a taper 23 to accommodate a ball head of known type shown in broken lines 23a.

FIG. 2 shows the various parts assembled together in position in a femur which is indicated in broken lines 24. The medial and lateral sleeve components 10 and 15 have been fastened in position so that the upper part of the bone canal is completely filled. As will be seen the proximal sleeve has an outer circumferential wall and comprises two proximal sleeve components each of which provides part of the circumferential outer surface of the sleeve.

In order to provide a modular construction two or more medial proximal sleeve components 10 of different dimensions and shapes are provided for alternative cooperation with medial side 12 of the stem and similarly two or more lateral proximal sleeve components 15 of different dimensions and shapes for alternative cooperation with the lateral side of the stem and/or neck portion are provided. Thus, the surgeon could have a large array of sleeve components in order to allow different combinations to be used together to provide a perfect fit.

A femoral prosthesis according to the invention can be supplied as a kit to surgeons in combination with a trial prosthesis. This ghost or trial prosthesis is identical with the femoral prosthesis and will be supplied with an array of identically shaped proximal sleeve components. Thus, the surgeon can assemble the trial prosthesis and use it as a trial. This enables him to alter the sleeve components until he achieves the fit which he desires. The femoral prosthesis can then be made up using the appropriate parts, the trial prosthesis removed and replaced by the femoral prosthesis itself.

In an alternative assembly, the ghost or trial prosthesis need consist only of the stem and/or shoulder/neck portion. The surgeon can use this stem to assemble the prosthesis sleeve components onto the trial stem until he achieves the result he requires, the trial prosthesis together with the selected sleeve portions can be removed from the bone canal and the sleeve components transferred to the stem and neck portion of the femoral prosthesis where they can be held in place as set forth above.

The invention enables the surgeon to fit a femoral prosthesis, especially after revision surgery, which provides a more effective cooperation with the bone than other known constructions.

Figure 3:
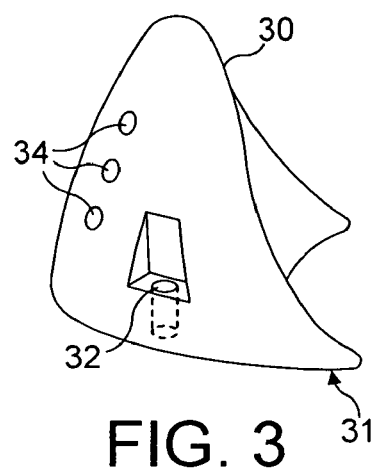
FIG. 3 is an isometric view of a greater trochanter support.

FIG. 3 shows a support for the greater trochanter and which is in the form of an upstanding curved horn 30. Lower surface 31 is flat so that it can be placed in position on the lateral proximal sleeve component 15. Bolt holes 32 are provided which enable horn 30 to be bolted down into position as shown in FIG. 4 by screws 33.

Figure 4:
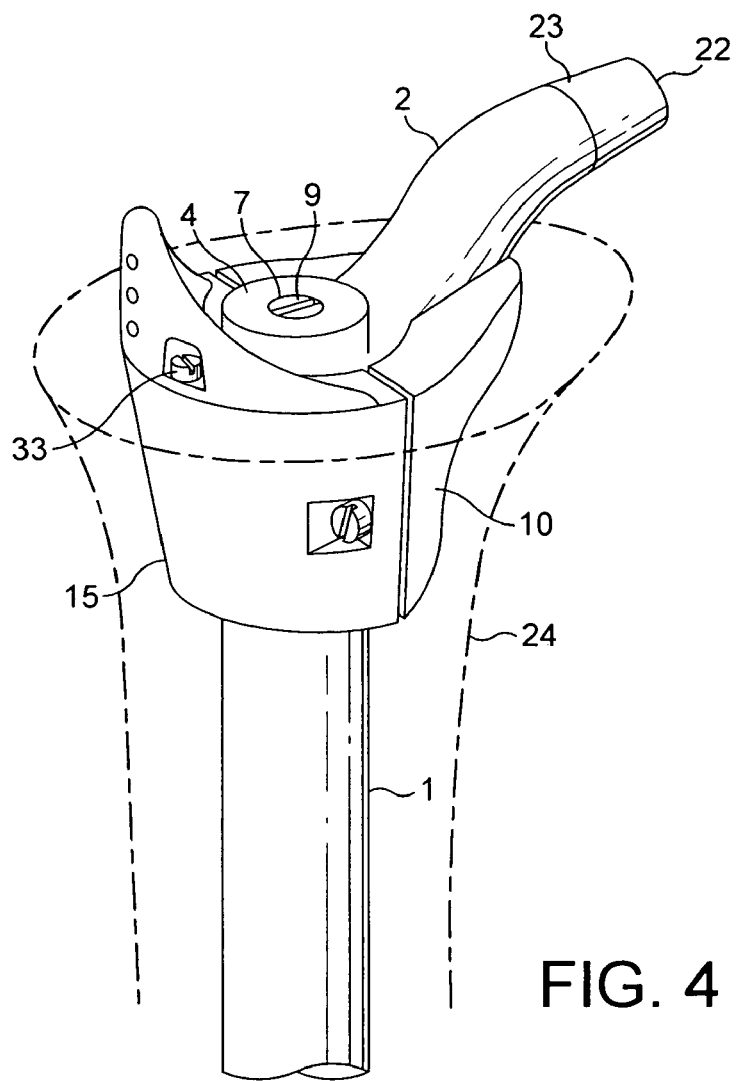
FIG. 4 is a similar view to that shown in FIG. 2 but with the greater trochanter support shown in FIG. 3 in position.

As will be seen from FIG. 4, horn 30 projects upwardly from sleeve component 15 to provide a support for the greater trochanter. Hire loop holes 34 are provided to allow the passage of a suitable filament or filaments which can be looped around the greater trochanter.

In the construction shown in FIGS. 3 and 4, the greater trochanter support is attachable to component 15 which thus enables it to be used in a modular way with the other components. However, if desired, it could be permanently and rigidly secured to the appropriate lateral proximal component. A ghost or trial combination of parts can again be provided as described with regard to the construction shown in FIGS. 1 and 2.

Figure 5:
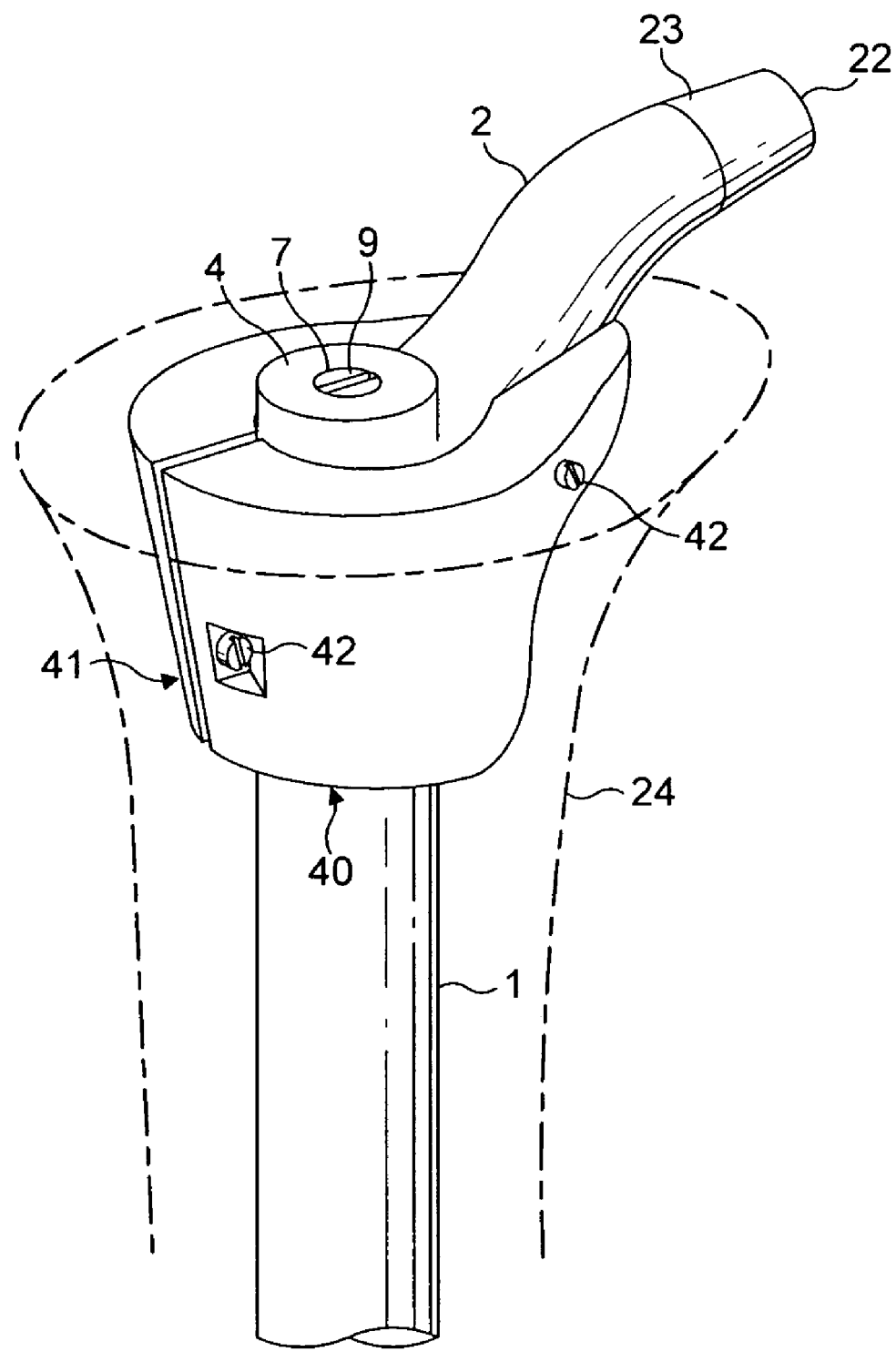
FIG. 5 shows another construction in which the proximal sleeve components are located respectively on the posterior and anterior sides of the stem.

In the construction shown in FIGS. 1 to 4, the proximal sleeve components are provided on the lateral and medial sides of stem 1 but FIG. 5 shows a construction in which there are two proximal sleeve components which are shaped and adapted to fit the posterior and anterior sides of stem 1. In FIG. 5 the same reference numerals are used to indicate similar parts to those shown in FIGS. 1 to 4. Reference numeral 40 indicates an anterior proximal sleeve component and reference numeral 41 indicates a posterior proximal sleeve component. The components are held together by screws 42 which act to pull the two components together and clamp them in position on stem 1. With this arrangement, grooves 11 and 14 and trough 13 are shown in the construction of FIG. 1 are split so that part of each groove and part of trough 13 are provided on each of the proximal sleeve components 40 and 41.

The construction acts in a similar way to that shown in FIGS. 1 and 2 and a number of proximal sleeve components 40 and 41 are provided so that the surgeon can form a proximal sleeve which fits the upper part of the bone canal. A support for the great trochanter, similar to that shown in FIG. 3 can also be included and which will straddle components 40 and 41. The construction of stem 1, shoulder 4 and neck 2 are similar to that shown in FIG. 1. Again, a ghost or trial combination of parts can be provided as described with regard to the construction shown in FIGS. 1 and 2.

Figure 6:
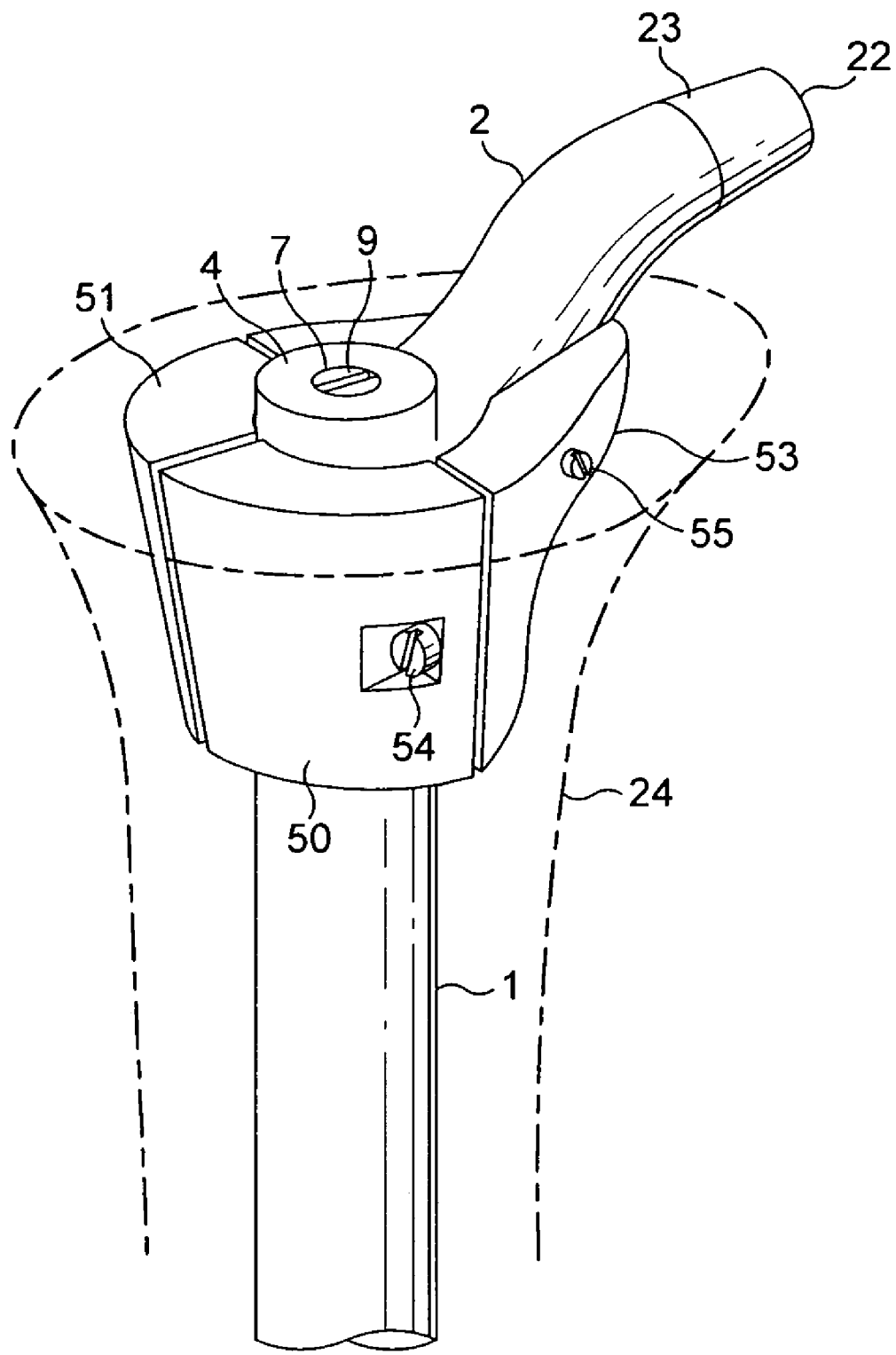
FIG. 6 shows another alternative construction in which three or four proximal sleeve components are employed.
Figure 7:
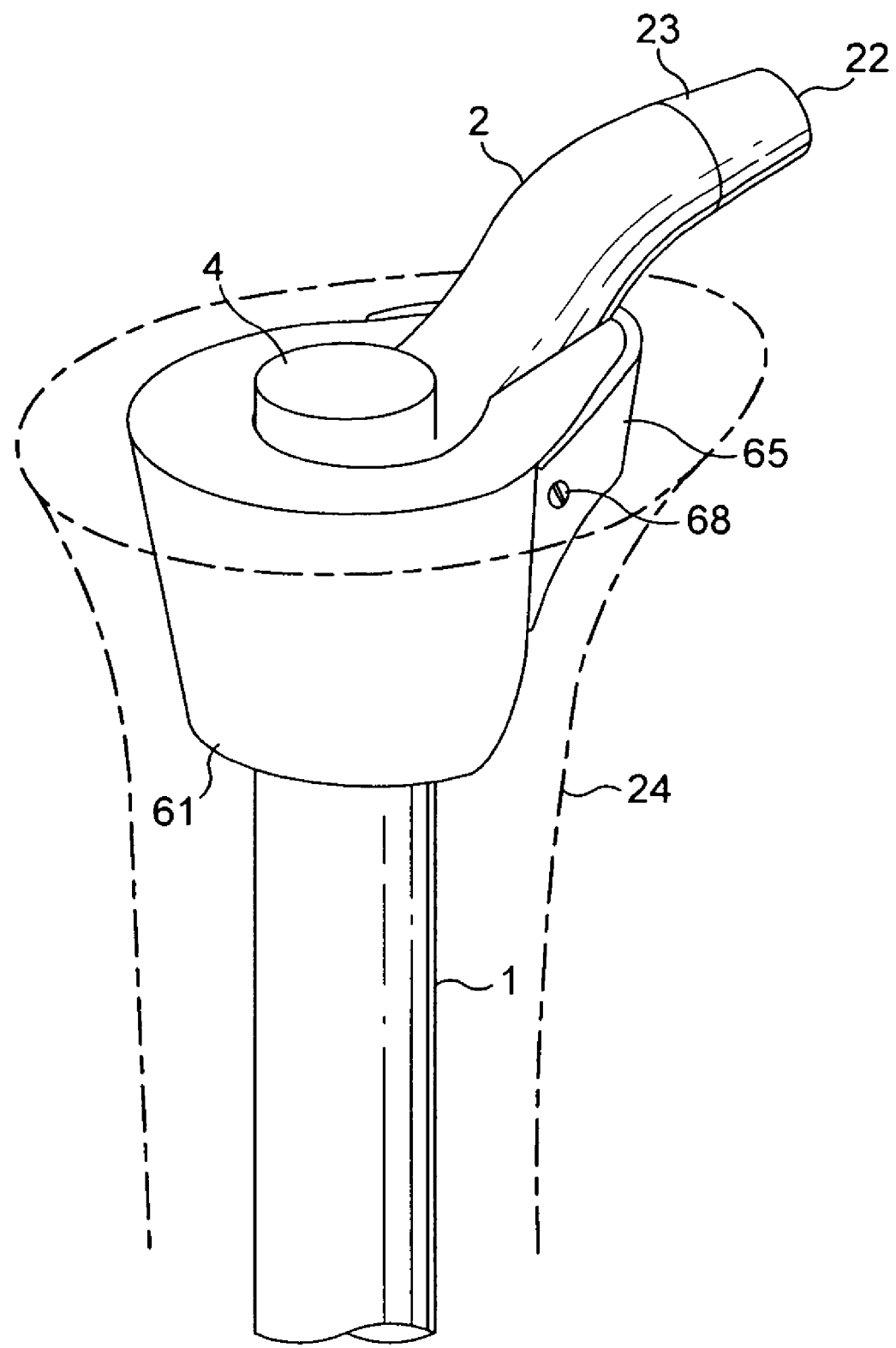
FIG. 7 is an isometric view from above of another alternative embodiment.

FIG. 6 shows another alternative construction but in this arrangement three proximal sleeve components are employed. The general construction of stem 1, shoulder 4 and neck 2 are similar to that shown in FIGS. 1 and 2 but the lateral proximal sleeve component 15 is replaced by an anterior proximal sleeve component 50 and a posterior sleeve component 51. Medial sleeve component 53 is similar to sleeve component 10 in FIGS. 1 and 2 but the circumferential length of its groove 11 is slightly less.

In this construction the circumferential length of the grooves on the inner surface of sleeve components 50 and 51 is also somewhat less than the groove in components 40 and 41 shown in FIG. 5 because the remainder of the contacting surface is provided by medial sleeve component 53. Sleeve components 50 and 51 are secured to medial sleeve component 53 by screws 54 which pass through openings in the sleeve components and extend into medial sleeve component 53. With this construction therefore three proximal sleeve components are provided. A number of each of sleeve components 50, 51, 53 are provided of different shapes and dimensions so that greater versatility in the shape of the proximal sleeve is achieved.

As mentioned above, in the construction shown in FIG. 6 three proximal sleeve components are used but it will be appreciated that the medial proximal sleeve component 53 could also be divided into two so that there would be four components. The two medial sleeve components could be connected together by a further screw indicated by broken lines 55. The construction shown in FIG. 6 with three components and also with four components enables the surgeon to compensate for irregularities between the sides of the bone canal. A ghost or trial combination of parts can again be provided as described with regard to the construction shown in FIGS. 1 and 2.

FIGS. 7, 8, 9 and 10 show another embodiment according to the invention. In the drawings, the same reference numerals are used to indicate similar parts to those shown in FIGS. 1 and 2 but in this arrangement the neck and stem are in one piece. This construction is most clearly shown in FIG. 8. If desired, such a one piece construction could also be used in the arrangements shown in FIGS. 1 to 6.

Figure 8:
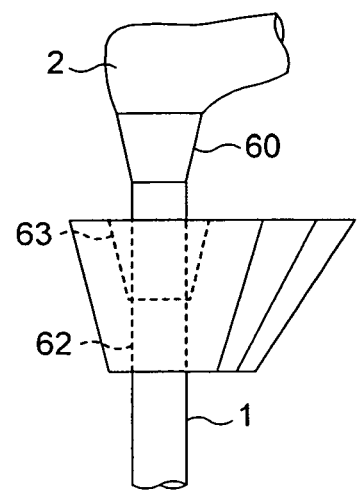
FIG. 8 is a side view of one of the proximal sleeve components.
Figure 9:
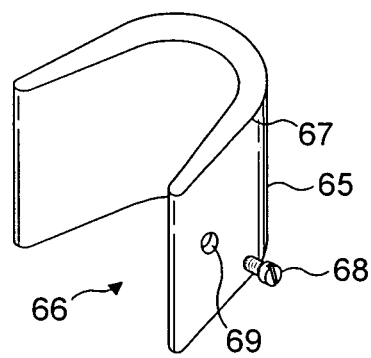
FIG. 9 is an isometric view of another proximal sleeve component.

In the construction shown in FIG. 8, however, the proximal end of stem 1 is provided with taper 60. This taper would, however, be unnecessary in the construction shown in FIGS. 1 to 6. The two proximal sleeve components are provided by a lateral proximal sleeve component 61 which also projects to the medial side, is appropriately tapered and has a bore 62. The proximal end of the bore has a taper 63 which is adapted to engage and lock onto taper 60 on stem 1. Thus, component 61 is fitted by sliding it over the stem and attaching it by tapers 60 and 63 by simple impaction. Trough 64 is provided to accommodate the distal portion of neck 2.

Figure 10:
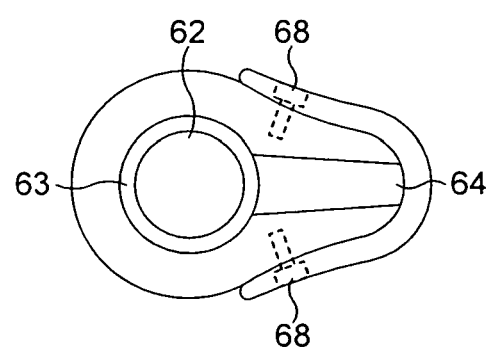
FIG. 10 is a plan view of the proximal sleeve components secured together.

In this construction a medial proximal sleeve component 65 is in the shape of a clamp having an inner groove 66 and a shaped outer surface 67. This clamp wraps around the medial side of lateral sleeve component 61 and is held in position by either a single screw 68 which passes through an opening 69 and into the lateral proximal sleeve component 61 or, as shown in FIG. 10, by two screws 68. As will be seen from the drawings two proximal sleeve components are again provided and again the surgeon can place appropriately shaped components in position to match the bone canal.

As with the other constructions a number of alternative sleeve components can be provided so that they can be placed in position to achieve the desired filling of the bone canal.

In the construction shown in FIGS. 7 to 10, taper 60 on the stem and the cooperating taper 63 on the sleeve component are arranged so that the component is placed over the stem and fixed into position but, alternatively, the direction of the tapers can be reversed and trough 64 could be provided as a slot extending right through sleeve component 61 so that the sleeve component could be fitted onto the stem from the reverse direction, that is over neck 2 thus enabling the sleeve components to be placed in position with the stem in the bone canal.

Figure 11:
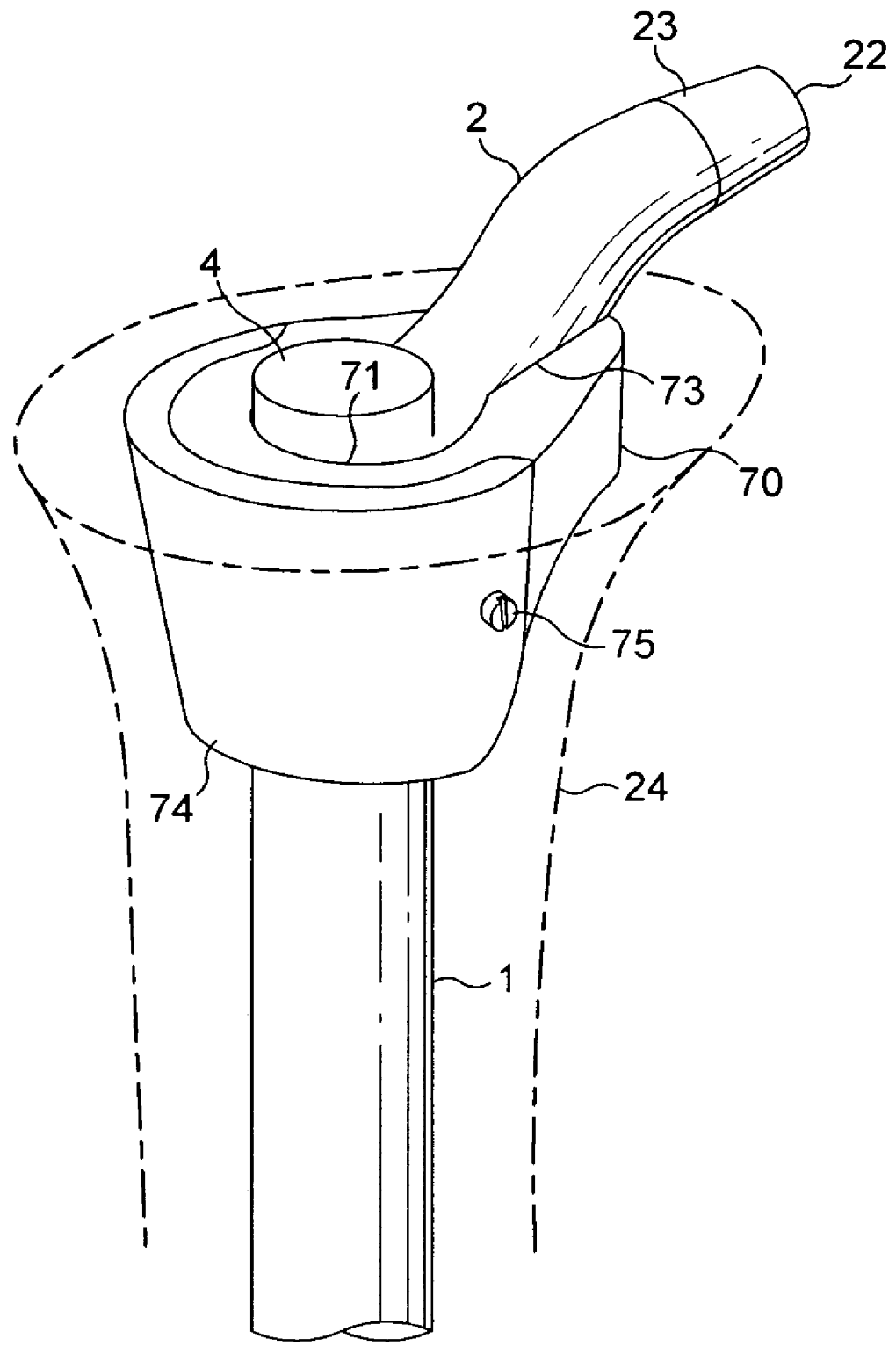
FIG. 11 is an isometric view of another alternative embodiment.

FIG. 11 shows another construction according to the invention which employs a medial proximal sleeve component 70 which has a bore 71 with a proximal tapered portion similar to that provided in lateral sleeve component 61 shown in FIGS. 7 to 10. The sleeve also has a taper similar to taper 60 shown in FIG. 8 so that medial sleeve component 70 is again located in position by mating tapers. A trough 73 accommodates neck 2. A lateral proximal sleeve component 74 engages around the lateral portion of component 70 and is held in place by screws 75.

This construction again enables the surgeon to provide a suitable shape to fill the proximal end of the bone canal and a number of medial and lateral proximal sleeve components 70 and 74 can be provided so as to create a modular construction of varying shapes. Again, with an appropriate construction a ghost or trial combination of parts can again be provided with the arrangements described with regard to the constructions shown in FIGS. 7 to 11.

Figure 12:
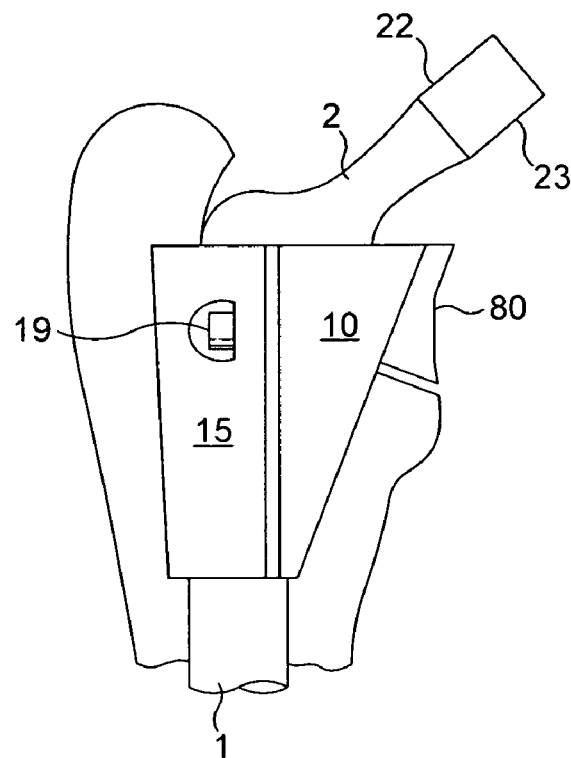
FIG. 12 is a side view of another alternative embodiment in place in a femur.

In certain femoral prostheses a collar is provided at the proximal end of the stem which can act as a "landmark" to seat the stem in the right position and which also prevents subsidence of the stem into the canal after fitting. The present invention also has provision to prevent such subsidence and to act as a "landmark" and this is provided by a projecting feature in the form of an abutment 80 as shown in FIG. 12 in which the same reference numerals are used to described similar parts as in FIG. 1.

Figure 13:
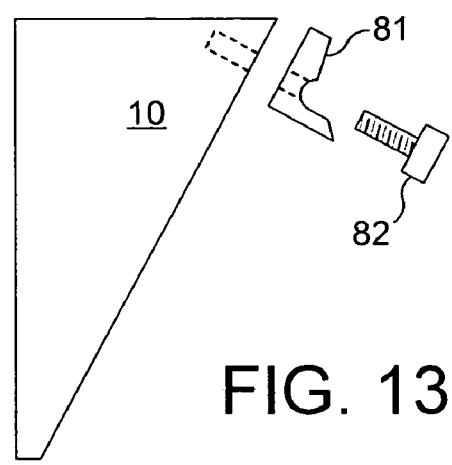
FIG. 13 is an exploded view of another alternative embodiment.

Abutment 80 can be formed integral with sleeve component 10 or, and alternatively, it can be provided as a separate modular abutment component 81 as shown in FIG. 13. The separate component 81 can be held in place by a screw or screws 82.

Components 10 which are provided with abutment 80 can again be provided in different sizes so that the abutment is appropriate to the bone with which it is to be used. Similarly, with the construction shown in FIG. 13 abutment components 81 can also be provided in different sizes so that they can be applied by the surgeon as required. Abutments or abutment components as described above can be provided on any of the arrangements described with regard to the other figures. The outer surfaces of the different parts of the apparatus can be coated or non-coated or have a specific surface texture. The surgeon can therefore choose not only the best fitting but also the best coating for each particular part.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral prosthesis comprising a stem for insertion in a femoral canal, a shoulder and a neck portion extending medially from a proximal stem portion and having a tapered trunion with a prosthetic femoral head, and a proximal sleeve having an outer circumferential surface and comprising at least two separate proximal sleeve components, each of which provides parts of the circumferential outer surface of the sleeve, and means for clamping the proximal sleeve components together in position on the proximal end of the stem, at least one portion of the proximal sleeve extending medially having a medially-laterally extending surface forming an arcuate trough which is open in the proximal direction for receiving a distal side of the neck portion.

2. The femoral prosthesis as set forth in claim 1 wherein said components are located respectively on the medial and lateral sides of the stem.

3. The femoral prosthesis as set forth in claim 2 wherein a lateral sleeve component is provided which also extends to the medial side of the stem and a medial sleeve component fastens to the lateral sleeve component to provide a clamp around the stem.

4. The femoral prosthesis as set forth in claim 3 wherein the lateral sleeve component includes a bore to surround the stem.

5. The femoral prosthesis as set forth in claim 4 wherein the bore is tapered to engage a cooperating taper on the stem.

6. The femoral prosthesis as set forth in claim 2 wherein a medial sleeve component is provided which also extends to the lateral side of the stem and a lateral sleeve component fastens to the medial sleeve component to provide a clamp thereon.

7. The femoral prosthesis as set forth in claim 6 in which the medial sleeve component includes a bore to surround the stem.

8. The femoral prosthesis as set forth in claim 7 wherein the bore is tapered to engage a cooperating taper on the stem.

9. The femoral prosthesis as set forth in claim 1 further comprising a means for separately attaching the shoulder and neck portion to the stem.

10. The femoral prosthesis as set forth in claim 9 wherein the attachable neck is located on a tapered portion on the proximal end of the stem.

11. The femoral prosthesis as set forth in claim 10 wherein the attachable neck is held in position on the tapered portion of the stem by a screw or clip.

12. The femoral prosthesis as set forth in claim 1 wherein said at least two sleeve components includes one or more sleeve components each of which is of the same interior shape but which has an alternatively shaped part-circumferential outer surface.

13. The femoral prosthesis as set forth in claim 1 wherein the neck portion is provided with means to attach a ball head.

14. The femoral prosthesis as set forth in claim 1 wherein a ball-shaped head is integral with the neck portion.

15. The femoral prosthesis as set forth in claim 1 wherein the means for securing the proximal sleeve portions include screws which engage the stem, or engage another proximal sleeve portion to allow said sleeve portions to be pulled together in tight engagement.

16. The femoral prosthesis as set forth in claim 1 wherein the proximal sleeve portions are arranged to clip onto the stem.

17. A kit for implanting a femoral prosthesis comprising:
a trial prosthesis including a trial stem for insertion into a femoral canal, a trial neck portion for coupling to and extending medially from the trial stem including a trunion with a prosthetic femoral head and at least two separate proximal sleeve portions, each having an outer circumferential surface, said at least two trial proximal sleeve components each providing part of the circumferential outer surface of a trial circumferential sleeve and screws for securing the trial proximal sleeve by clamping the components around the stem in position at the proximal end of the trial stem, one proximal sleeve portion having an arcuate medially-laterally extending surface open in the proximal direction for receiving the neck; and
a plurality of prosthetic femoral components.

18. The kit as set forth in claim 17 further including neck portions separately attachable to a stem portion of each femoral component wherein the trial prosthesis includes a similar attachable trial stem portion to allow a femoral prosthesis to be constructed which is identical with the trial prosthesis.

19. The kit as set forth in claim 17 wherein the trial stems for insertion in a femoral canal and the trial shoulder and neck portions are dimensioned and shaped to receive the proximal sleeve portions of the femoral prosthesis, and said screws detachably secure them in place at the proximal end of the trial stem.

20. The kit as set forth in claim 19 wherein a separate and attachable neck portion is provided on the trial prosthesis.

21. A femoral component for implantation in the medullary canal of the femur comprising:
a stem having a proximal portion with a circumferential outer surface and a medially extending neck portion including a trunion with a prosthetic head;
at least two separate sleeve portions mounted on the proximal stem portion and surrounding at least part of said circumferential outer surface, each said sleeve portions having an outer surface for placement adjacent an inner surface of the medullary canal and an inner surface for placement adjacent the stem outer surface at least one of the sleeve portions having a medially-laterally extending arcuate surface forming a trough on a proximal surface for receiving a distal surface of the neck portion the trough being open in a proximally facing direction; and engageable clamping elements on each of said at least two sleeve portions for clamping the sleeve portions to the proximal stem portion.

22. The femoral component as set forth in claim 21 wherein said portions are located respectively on the medial and lateral sides of the stem.

23. The femoral component as set forth in claim 22 wherein one of the two sleeve portions includes a threaded bore and the sleeve portions are clamped around the proximal stem portion with screws.

* * * * *

UNITED STATES PATENT AND TRADEMARK OFFICE
CERTIFICATE OF CORRECTION

PATENT NO. : 7,491,242 B2
APPLICATION NO. : 10/795946
DATED : February 17, 2009
INVENTOR(S) : Pichon et al.

It is certified that error appears in the above-identified patent and that said Letters Patent is hereby corrected as shown below:

Column 7, line 47, "said components" should read --said sleeve components--.
Column 10, line 2, "said portions" should read --said sleeve portions--.

Signed and Sealed this

Twentieth Day of April, 2010

David J. Kappos
*Director of the United States Patent and Trademark Office*